United States Patent [19]

Lillwitz

[11] Patent Number: 4,739,108
[45] Date of Patent: Apr. 19, 1988

[54] PURIFICATION AND ESTERIFICATION OF METHACRYLIC ACID

[75] Inventor: Lawrence D. Lillwitz, Glen Ellyn, Ill.

[73] Assignee: Amoco Corporation, Chicago, Ill.

[21] Appl. No.: 623,946

[22] Filed: Jun. 25, 1984

[51] Int. Cl.⁴ .................................................. C07C 67/08
[52] U.S. Cl. .................................. 560/205; 560/218; 562/600; 562/606; 203/80; 203/DIG. 21
[58] Field of Search ................. 560/205, 218; 562/600; 203/DIG. 21, 80

[56] References Cited

U.S. PATENT DOCUMENTS

| | | | |
|---|---|---|---|
| 3,392,191 | 7/1968 | Ensor et al. | 560/205 |
| 3,639,460 | 2/1972 | Wenzel et al. | 560/205 |
| 3,951,756 | 4/1976 | Dirks et al. | 560/218 |
| 4,040,913 | 8/1977 | Clovia et al. | 562/600 |
| 4,250,328 | 2/1981 | Fujita et al. | 560/205 |

Primary Examiner—Donald B. Moyer
Assistant Examiner—L. Hendriksen
Attorney, Agent, or Firm—James R. Henes; William H. Magidson; Ralph C. Medhurst

[57] ABSTRACT

A process is disclosed for separation of propionic acid and methacrylic acid and esterification of methacrylic acid with an aliphatic alcohol of from 1 to 4 carbon atoms in presence of a suitable catalyst wherein separation and esterification is obtained with minimal polymerization of methacrylic acid.

7 Claims, No Drawings

PURIFICATION AND ESTERIFICATION OF METHACRYLIC ACID

FIELD OF THE INVENTION

This invention relates to an improved method for purification and esterification of methacrylic acid.

Methyl methacrylate is a large volume chemical prepared by esterification of methacrylic acid. Recently interest has developed in production of methyl methacrylate by a process entailing the reaction of propionic acid and formaldehyde to form methacrylic acid. The process results in a mix of methacrylic acid and propionic acid, as well as other by-products. After separation of the methacrylic acid from propionic acid, the methacrylic acid is esterified to form methyl methacrylate.

However, the separation of methacrylic acid and propionic acid by usual methods is difficult. Methacrylic acid polymerizes readily upon the application of heat if distilled. Addition of inhibitors such as phenothiazine, benzoquinone, hydroquinone, and para-phenylenediamine, which require use of oxygen to be effective, can reduce polymerization of methacrylic acid. However, these inhibitors are expensive and they must eventually be separated and disposed of. Accordingly, it is preferable either to not use inhibitors or to use minimal quantities.

Esterification of methacrylic acid with methanol in the presence of propionic acid and a suitable catalyst to form methyl methacrylate also leads to formation of unwanted methyl propionate. Therefore, it is essential for propionic acid to be separated from methacrylic acid prior to contacting with methanol and a catalyst.

I have invented a process for separation of propionic acid, methacrylic acid and an alkyl methacrylate, preferably methyl methacrylate, wherein propionic acid is distilled off from the methacrylic acid, methacrylic acid polymerization is minimized and methacrylic acid is esterified in a transfer line reactor with a short chain aliphatic alcohol of the formula ROH wherein R is an alkyl group of from 1 to 4 carbon atoms. The alkyl methacrylate, preferably methyl methacrylate, and propionic acid are distilled overhead together. Esterification results in the production of water. Propionic acid and water form an azeotropic mixture which boils at 99° C. and atmospheric pressure. Methyl methacrylate and water form an azeotropic mixture which boils at 83° C. and atmospheric pressure. Therefore, the overhead product is easily separated by conventional means.

The esterification of methacrylic acid with an alcohol in the presence of an esterification catalyst is known in the art. Sulfuric acid or sulfonic acids such as p-toluene sulfonic acid have been principally used as catalyst for the esterification. As to the amount in which these catalysts are employed, U.S. Pat. No. 3,639,460 teaches that a quantity of $SO_3$ is to be used, introduced in the form of sulfuric acid or sulfonic acids, which is 8 to 30 (wt) % of the methacrylic acid present in the reactor. The transfer line reactor in effect comprises a sump of the distillation column into which equivalent amounts of the acid and esterifying alcohol are introduced at a rate equivalent to the formation of the ester. The ester is removed in an azeotropic admixture with water and with excess methanol.

It is an object of this invention to provide a process for separation of propionic acid from methacrylic acid wherein polymerization of methacrylic acid is minimal.

It is a further object of this invention to provide a process for the production of methacrylic esters.

Another object of this invention is to provide a process for the production and separation of a methacrylic ester in the presence of water and propionic acid wherein the feed stream contains propionic acid and methacrylic acid.

Another object of this invention is to provide a process for the production of a methacrylic ester wherein water generated by the esterification reaction preferentially forms an azeotropic admixture with methyl methacrylate, thus permitting easy separation of the methacrylate ester in the overhead from propionic acid.

SUMMARY OF THE INVENTION

Disclosed is an improved process for purification and esterification of methacrylic acid wherein the feed stream contains methacrylic acid and propionic acid. The propionic acid is distilled concurrently with an azeotrope of an alkyl methacrylate, preferably methyl methacrylate, formed in a transfer line reactor or sump reactor. In preparing methyl methacrylate, dilution of the methyl methacrylate water azeotrope with propionic acid aids in preventing polymerization of methyl methacrylate. The methacrylic acid in the transfer line reactor or sump reactor is diluted to less than 85 (wt) % by the sulfuric acid catalyst, methyl alcohol, water and methyl methacrylate to minimize polymerization of methacrylic acid. The methacrylic acid is esterified in the transfer line reactor or sump reactor at a temperature of about 115°–120° C. to form an 85 (wt) % methyl methacrylate:15 (wt) % water azeotrope. Propionic acid and methyl methacrylate:water azeotrope is distilled overhead at a temperature of 81°–85° C. and pressure of 100 mm Hg. The overhead stream of propionic acid and methyl methacrylate:water azeotrope is further distilled to separate the azeotrope and propionic acid. The propionic acid can be recycled to the propionic acid:formaldehyde reactor to form methacrylic acid.

DETAILS OF THE INVENTION

The process of the instant invention relates to a process for purification and esterification of methacrylic acid wherein the methacrylic acid stream contains propionic acid. In the process of the instant invention, the propionic acid and methacrylic acid are not separated prior to being distilled. The methacrylic acid esterification reactor can be a transfer line reactor. Methacrylic acid polymerizes extensively at the temperatures required to separate propionic acid and methacrylic acid.

In the preparation of methacrylic acid by the reaction of propionic acid and formaldehyde, excess unreacted propionic acid is present. It is an advantage of the present invention that the excess propionic acid is recovered for recycle to the propionic acid:formaldehyde reactor.

Methacrylic acid is continuously esterified with an aliphatic alcohol of 1 to 4 carbon atoms in high yields with concentrated sulfuric acid or a sulfonic acid of the formula $RSO_3H$ wherein R is $C_6H_5-$, $-C_6H_4CH_3$, $-C_6H_4SO_3R'$ and R' is $-H$, $-CH_3$, $-C_2H_5$ or $-C_3H_8$, or a mixture of these acids. The aliphatic alcohol of from 1 to 4 carbon atoms, among others, can be methanol, ethanol, propanol, n-butanol or isobutanol. Methanol is preferred in the process of the invention. Methacrylic acid is separated from propionic acid at a temperature of 85°–91° C. and 110 mm Hg, and is thereupon reacted with alcohol in the presence of sulfuric acid or sulfonic acid at a temperature of 115°–120° C. and 130 mm Hg. Methyl methacrylate, formed with methanol, forms an azeotrope of 85 (wt) % methyl methacrylate and 15 (wt) % water with the water produced by the esterification reaction. The lower boiling point of the methyl methacrylate-water azeotrope causes the azeotrope to distill as overhead at 81°–85° C. and 100 mm Hg.

The instant invented process is a process for esterification of methacrylic acid and separation of propionic acid from methacrylic acid which effectively separates the two feed stream components without extensive polymerization of the methacrylic acid.

In a preferred method, methyl alcohol is reacted in a transfer line reactor with methacrylic acid on a 1:1 mole base. Water resulting from esterification forms an azeotrope with methyl methacrylate so produced of about 85 (wt) % methyl methacrylate and 15 (wt) % water.

The instant invention accordingly comprises a process for esterification of methacrylic acid in the presence of a suitable catalyst under reaction conditions with an alcohol wherein the acid compound:alcohol mole ratio is from about 0.4:1.2 to about 1.0:1.2, preferably from about 0.9:1.2 to about 1.0:1.2, at a temperature within the range of from about 50° C. to about 130° C. and pressures of from 50 to 250 mm Hg, and the feed stream contains propionic acid.

It is essential that the acid compound: alcohol mole ratio not be greater than 1:1 because the acid compound therefore would accumulate in the bottom of the distillation tower.

In summary, the instant invention comprises a process for separation of methacrylic acid from propionic acid and esterification of methacrylic acid with an aliphatic alcohol of from 1 to 4 carbon atoms in the presence of a suitable catalyst wherein methacrylic acid:alcohol mole ratio is from about 0.4:1.2 to about 1:1.2 at a temperature of from about 50° C. to about 130° C. and a pressure of from about 50 mm Hg to about 250 mm Hg which process comprises: (a) injecting said methacrylic acid and propionic acid into a distillation column of at least 40 trays at a temperature within the range of from about 50° C. to about 130° C., (b) said propionic acid being removed as overhead from said column, (c) said methacrylic acid, as column bottoms, being reacted with said alcohol in presence of said catalyst wherein said methacrylic acid is less than 85 (wt) % of said acid, alcohol, catalyst mix, at a temperature of from 50° C. to about 130° C. and a pressure of from about 50 mm Hg to about 250 mm Hg to form an ester of methacrylic acid, (d) said ester forming a water:ester azeotrope, (e) said water:ester azeotrope removed as an overhead mixture with said propionic acid.

The invention will be illustrated by reference to the following specific examples.

EXAMPLE I

Two 20-tray 1-inch Oldershaw distillation columns were stacked together with a feed line at tray 20. The transfer line reactor was a 200 cc flask which had a burette attached through a side arm, the tip of the burette extending below the liquid level in the 200 cc distillation flask. The burette was filled with methyl alcohol. The transfer line reactor contained 10 g of concentrated (98%) sulfuric acid as catalyst and 50 g of methacrylic acid. A feed consisting of 85/15 (wt%) propionic acid (PA):methacrylic acid (MA) and 1000 ppm phenothiazine was fed into the distillation system at a rate of 156 g/hr for 5 hours. At the top of the column the temperature was 81°–85° C. at 100 mmHg. Temperature at the feed line was 85°–91° C. at 110 mmHg. Temperature at the distillation reboiler was 115°–120° C. at 130 mmHg. Methyl alcohol was fed through the burette into the transfer line reactor based on a stoichiometric ratio with the methacrylic acid fed into the system. A water azeotrope of methyl methacrylate (MMA) was removed as overhead. Propionic acid from the feed was also removed as overhead. Analysis of the organics in the overhead was 84% PA, 13.4% MMA, 1.4% MA and 1% methyl propionate. After completion of this experiment the reboiler was shown to contain only 1.67 g of solids.

The presence of methacrylic acid and methyl propionate in the distillation overhead of Example I indicated incomplete separation of methyacrylic acid from propionic acid in distillation column. This separation is improved with more controlled operation. Example II demonstrates this point.

EXAMPLE II

A large (2 inch) distillation apparatus which consisted of 40 Oldershaw trays (20 trays above and 20 trays below the feed tray) was erected for the separation of methyacrylic acid and propionic acid. The transfer line reactor consisted of a ¼" recirculation line which was pumped through a heated oil bath to supply heat to the system. A feed consisting of approximately 80/20 (wt) % propionic acid: methacrylic acid was fed to the distillation system at 300–400 g/hr. At the top of the column the temperature was 86° C. at 100 mm Hg. Temperature at the feed tray was 88° C. at 110 mm Hg. Temperature at the transfer line reactor was 113°–114° C. at 130 mm Hg. After several hours of running to attain steady-state conditions in the column the overhead propionic acid stream contained 0.2 (wt) % methacrylic acid, and the bottom methacrylic acid stream contained 0.05 (wt) % propionic acid.

The ease of separating the methyl methacrylate:water azeotrope from the propionic acid contained in the overhead product in Example I will be demonstrated in Example III.

EXAMPLE III

A 300 g feed stream mixture was prepared of the overhead received from distillation and esterification of methacrylic acid as in Example I. Composition of the mixture was:

|  | Wt (g) | % |
| --- | --- | --- |
| Propionic acid (PA) | 249 | 83 |
| Methyl propionate (MPA) | 2.4 | 0.8 |
| Methyl methacrylate (MMA) | 38.4 | 12.8 |
| Methacrylic acid (MA) | 3 | 1.0 |
| Water | 7.5 | 2.5 |
| Phenothiazine | 100 ppm | |

The above mixture was distilled in a 20-tray 1-inch Oldershaw column fitted with a liquid dividing head and a take off system fitted with ice and dry ice traps. The overhead pressure was kept at 200 mm Hg and the reflux ratio was 2. The results were as follows:

| | Conditions | |
| --- | --- | --- |
| Times | Pot | Ovhd. |

-continued

| Minutes | °C. | °C. |
|---|---|---|
| 0 | 81.5 | |
| 33 | 81.5 | 46 |
| 50 | 97 | 46 |
| 60 | 99 | 48 |
| 77 | 102.5 | 57 |
| 86 | 103 | 93 |
| 93 | 104 | 100 |
| 132 | 106 | 102 |
| 170 | 106 | 102 |
| 193 | 150+ | 101 |

Results

| Times Minutes | Ovhd. g | MPA | MMA + H$_2$O | PA | MA |
|---|---|---|---|---|---|
| 0 | | | | | |
| 33 | — | — | — | — | — |
| 50 | — | — | — | — | — |
| 60 | 17.00 | 9.5 | 90.5 | 0 | 0 |
| 77 | 20.10 | 2.0 | 98.0 | 0 | 0 |
| 86 | 7.39 | 1 | 76.5 | 21.0 | 0 |
| 93 | 13.59 | 0.2 | 14 | 86 | 0.3 |
| 132 | 97.57 | 0.02 | 2.5 | 97 | 2.7 |
| 170 | 99.15 | 0 | 0.07 | 99.2 | 0.7 |
| 193 | 31.71 | 0 | 0 | 97.5 | 1.4 |
| | 286.51 | | | | |
| Pot residue | 10.49 | | | | |
| Total | 297.0 | | | | |

The above data indicate that methyl mechacrylate and water are easily separated from propionic acid at temperatures of 48°–100° C. and 200 mmHg.

What is claimed is:

1. A process for separation of methacrylic acid from propionic acid and esterification of said methacrylate acid with an aliphatic alcohol of from 1 to 4 carbon atoms in the presence of a suitable catalyst which process comprises: (a) injecting said methacryltic acid and propionic acid into a distillation column of at least 40 trays, (b) distilling said propionic acid and a portion of said methacrylic acid as overhead from said column at a temperature within the range of from about 50° C. to about 130° C. and a pressure of from about 50 mm Hg to about 250 mm Hg, (c) reacting remaining portion of said methacrylic acid, as column bottoms, in a transfer line reactor or sump with said alcohol wherein said methacrylic acid:alcohol mole ratio is from about 0.4:1.2 to about 1:1.2 in presence of said catalyst wherein said methacrylic acid in said transfer line reactor or said sump is less than 85 (wt) % of said acid, alcohol and catalyst mix, at a temperature of from about 50° C. to about 130° C. and a pressure of from about 50 mm Hg to about 250 mm Hg to form an ester of methacrylic acid, (d) forming a water:ester azeotrope in said transfer line reactor or said sump with water of said esterification reaction, (e) removing said water:ester azeotrope at a temperature of from about 50° C. to about 130° C. and a pressure of from about 50 mm Hg to about 250 mm Hg from said distillation column as an overhead mixture with said propionic acid, (f) distilling said water:ester azeotrope and propionic acid to separate said azeotrope and propionic acid in a separate distillation column.

2. The process of claim 1 wherein said alcohol is selected from the group consisting of methanol, ethanol, propanol, n-butanol and isobutanol.

3. The process of claim 1 wherein said alcohol is methanol.

4. The process of claim 1 wherein said methacrylic acid is reacted with said alcohol in a transfer line reactor.

5. The process of claim 1 wherein said methacrylic acid:alcohol mole ratio is from about 0.9:1.2 to about 1.0:1.2.

6. The process of claim 1 wherein said catalyst is selected from the group consisting of sulfuric acid and a sulfonic acid of the formula RSO$_3$H wherein R is selected from the group consisting of C$_6$H$_5$—, —C$_6$H$_4$CH$_3$, —C$_6$H$_4$SO$_3$R$^1$ and R$^1$ is —H, —CH$_3$, —C$_2$H$_5$ or —C$_3$H$_8$ or a mixture thereof.

7. The process of claim 1 wherein said catalyst is sulfuric acid.

* * * * *